(12) United States Patent
Jacobs (10) Patent No.: US 8,763,479 B1
(45) Date of Patent: Jul. 1, 2014

(54) MOLD AND SENSOR CELLS FOR A NANOCOMPOSITE MATERIAL PROCESS CONTROL SYSTEM

(75) Inventor: John David Jacobs, West Chester, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 164 days.

(21) Appl. No.: 13/158,970

(22) Filed: Jun. 13, 2011

Related U.S. Application Data (60) Provisional application No. 61/353,704, filed on Jun. 11, 2010.

(51) Int. Cl.
*G01N 37/00* (2006.01)
(52) U.S. Cl.
USPC .................................................. 73/864.91

(58) Field of Classification Search
USPC .............. 73/864.91, 502, 503, 547, 551, 718, 73/724
See application file for complete search history.

(56) References Cited

U.S. PATENT DOCUMENTS

| | | | | |
|---|---|---|---|---|
| 5,201,228 A | * | 4/1993 | Kojima et al. | ................... 73/724 |
| 2008/0196517 A1 | * | 8/2008 | Harvey et al. | .............. 73/864.91 |

* cited by examiner

*Primary Examiner* — Lisa Caputo
*Assistant Examiner* — Brandi N Hopkins
(74) *Attorney, Agent, or Firm* — AFMCLO/JAZ; Fredric Sinder (57) ABSTRACT

Two new sample cells for use with a new nanocomposite material process system are described. A new computer automated processing system incorporates integrated impedance spectroscopy sensing and electric directed morphology, particularly for use with new nanocomposite materials. The two new mold and sensor cells solve the problem of sample deformation during curing by adding a vented cavity behind the electrodes; and, the problem of air entrapment and bubble formation in a sample by providing a channel for injecting the sample from top to bottom.

4 Claims, 8 Drawing Sheets

MOLD AND SENSOR CELLS FOR A NANOCOMPOSITE MATERIAL PROCESS CONTROL SYSTEM

RIGHTS OF THE GOVERNMENT

The invention described herein may be manufactured and used by or for the Government of the United States for all governmental purposes without the payment of any royalty.

CROSS REFERENCE TO RELATED PATENT APPLICATION

This application claims priority under 35 U.S.C. §119(e) from U.S. provisional application 61/353,704, filed Jun. 11, 2010, and titled "Nanocomposite Material Process Control System with Online Impedance Spectroscopy and Electric-Field Action." The invention description contained in that provisional application is incorporated by reference into this description.

BACKGROUND OF THE INVENTION

The present invention relates generally to process control systems, particularly to a process control system for optimizing process parameters for nanocomposite materials, and specifically to sample cells for a nanocomposite material process control system.

Advanced materials, such as polymer nanocomposites, serve as innovative structural elements while offering a host of value-added features and multifunctional properties.

Relatively little attention has been placed on pioneering new process control, sensor and in situ control techniques to enhance observability and controllability of key physiochemical changes that occur over a wide range of time- and length-scales during processing of these new advanced materials. Complexity, practicality and tradition have limited many conventional process control approaches to simple environmental control protocols such as staged environmental conditions (temperature, pressure, mass flow, etc.) based on laborious and time consuming factorial tests and offline validation. This works for many conventional material systems, but for advanced materials where critical properties depend on local structure and the synergistic effects of matrix/nanofiller interfaces, this approach is complicated, inefficient and unproductive.

As described in J. D. Jacobs, "Online Impedance Spectroscopy of Thermoset Nanocomposites for Materials In Situ Process Control," PhD. Dissertation, Electrical Engineering, University of Cincinnati, Cincinnati, 2009, included as part of provisional application 61/353,704 and fully incorporated by reference into this patent specification, the inventor has developed a computer automated processing system with both integrated impedance spectroscopy sensing and electric field directed morphology. This system is the first to successfully incorporate multi-sensor impedance spectroscopy as an online characterization component in a comprehensive computer automated system for processing nanoclay/epoxy thermosets in a controlled and repeatable process; and, also induce field-aligned morphology of intercalated nanoclay by applied quasi-static electric fields.

This new material process control system establishes a development platform for overcoming common limitations suffered by conventional material processing practices by combining environmental control (computer automated temperature and pressure), online impedance spectroscopy (non-destructive, multi-sensor, multi-length-scale information), and electric-field actuation into one computer controlled system. This approach to material process control, particularly for use with nanocomposites and other advanced material fabrication processes, provides a novel set of powerful tools for sustained, repeatable synthesis and development of next-generation feedback process control methods where online strategies may be a prerequisite for obtaining material products with important value-added or tailored physical/chemical properties. In contrast to conventional processing techniques, electric-field actuation techniques provide a novel means for designing materials, particularly directed morphology of layered silicate/epoxy thermosets) with anisotropic properties.

The ability to perform online impedance/dielectric sensing and characterization during a material processing cycle has a multifold impact.

First, the system provides a rich set of time-dependent information at a continuum of length-scales and frequencies in a non-destructive, non intrusive way by use of embedded and/or surface mountable sensors. The use of impedance spectroscopy as a sensor is a well-known electrical characterization technique capable of probing a wide range of molecular and charge transfer phenomena, which in turn can provide direct, repeatable information regarding the state of cure, interfacial/morphological characteristics, and other important material related properties.

Second, online sensor data facilitates an ability to discover and develop advanced feedback process control strategies useful for optimizing material manufacturing by minimizing cure cycle time, material variability, and establish correlations between online data and desired material properties. This also provides a way to shift labor- and time-intensive QA/QC tasks, typically performed by offline validation measurements, into a "feedback loop" where sensor data can potentially indicate deviations in a real time manner to minimize feedstock waste and processing time; and, where corrective measures may be applied automatically to guide the material processing towards a goal product.

Effective manufacturing of emerging material systems requires the assurance of reproducibility and quality. Reaching goals of simplifying processing cycle optimization, and minimizing batch variability and costs associated with feedstock waste, requires comprehensive monitoring and control using innovative strategies that operate within the boundaries of the process. Therefore, new development opportunities exist for online sensor/control techniques to help identify and realize the full performance potential of a material system.

Two very critical components of any such processing system are the sample mold and sensor cells for holding and instrumenting materials being processed. Typical problems include sample deformation during curing from thermal expansion and air entrapment and bubble formation.

It is, therefore, an object of the present invention to provide new and improved sample cells particularly adapted for use in a nanocomposite material process control system.

SUMMARY OF THE INVENTION

The present invention answers the described need for new and improved sample cells for use with a nanocomposite material process control system by providing:

(a) a new injection mold and sensor cell: and, (b) a new compression mold and sensor cell.

What's new in the present invention includes solving the problem of sample deformation during curing from thermal expansion by adding a vented cavity behind the electrodes;

and, solving the problem of air entrapment and bubble formation in a sample by providing a channel for injecting the sample from top to bottom.

Accordingly, the present invention is directed to a sample cell having a cell housing, a pair of spaced electrodes embedded inside the cell housing, a sample cavity between a front face of each of the spaced electrodes for holding a material sample, an expansion cavity behind a back face of at least one of the spaced electrodes, and a vent channel from the expansion cavity to the outside of the cell housing.

The present invention is additionally directed to a sample cell having a cell housing having a top and a bottom, a pair of spaced electrodes embedded inside the cell housing, a sample cavity between a front face of each of the spaced electrodes for holding a material sample, an injection channel through the cell housing from the top of the cell housing into the bottom of the cavity; and, a separator between the spaced electrodes, wherein the injection channel is formed within the separator, and further wherein the he separator comprises two pieces and the injection channel is formed between the two pieces. The sample cell may also include an expansion cavity behind a back face of at least one of the spaced electrodes, and a vent channel from the expansion cavity to the outside of the cell housing.

DETAILED DESCRIPTION

The two new mold and sensor cells, or sensor molds, of the present invention primarily comprise two parallel copper plate electrodes embedded inside a silicone mold. The purpose of this arrangement is two-fold. First, it provides a robust means for acquiring repeatable impedance measurements as this geometric configuration creates a uniform field perpendicular to the plates. Fringe field errors from peripheral capacitance can be kept small when the ratio of diameter to plate spacing is greater than 10 to 1. The electrodes also serve a dual purpose of applying high-strength electric-fields. Other sensor configurations are possible. For example, miniature interdigitated conductive arrays may be used to provide localized information by way of fringe-field surface measurements.

Two types of sensor molds were developed for this work, an injection mold and sensor cell and a compression mold and sensor cell.

The injection mold and sensor cell is designed for low-viscosity materials where the pre-cure suspension can be injected using a syringe, typically composites cured with EPIKURE W. This sensor cell design comprises silicone mold halves that provide a cylindrical sample cavity. Cut-outs exist for the copper electrodes and for a material injection pathway at the top of the mold which provides a pathway, or channel, to fill the sample void from bottom-to-top to minimize air entrapment. A second pathway along the center of the mold provides a vent for air and sample overflow. Reinforcing aluminum plates on front and back exterior faces promote a liquid-tight seal and a more uniform distribution of heat across the cell.

The compression mold and sensor cell was developed for higher viscosity materials where direct injection is not possible. For this application, the material is loaded using a hot-air gun to soften and compress the material into the sample cavity. The described example embodiment sensor mold was used for composites cured with sulfanilamide, but the concept applies, of course, to any high viscosity material.

Figure 1:
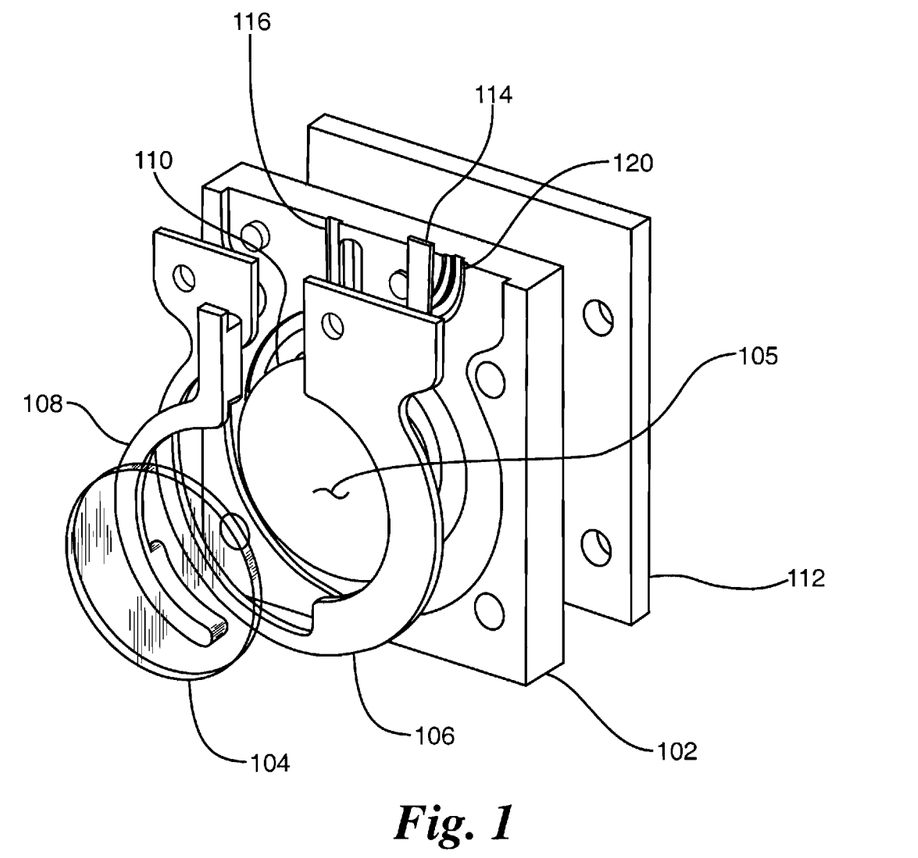
FIG. 1 is an exploded view of the back half of an example embodiment of an injection mold and sensor cell according to the teachings of the present invention.
Figure 4:
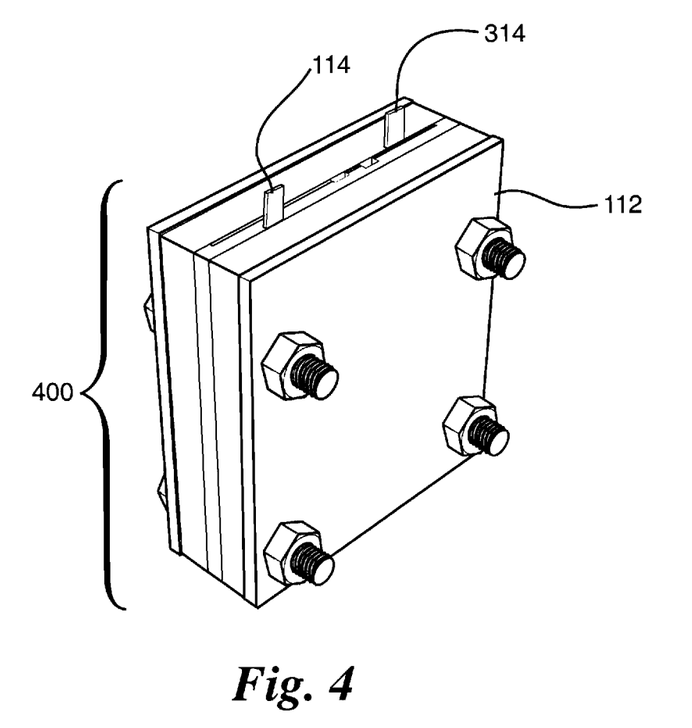
FIG. 4 is an assembled view of the injection mold and sensor cell of FIG. 1.

FIG. 1 is an exploded view of the back half of an example embodiment of a low viscosity material injection mold and sensor cell 400, shown fully assembled in FIG. 4. The back half comprises a back silicone mold half 102 for holding a nanocomposite sample 104 in a cavity formed by TEFLON inserts 106 and 108. A back copper electrode 110 contacts the back of sample 104 and includes an electrode tab 114 for electrical connections. An aluminum reinforcing back plate 112 provides structural support. The back half of an injection port 116 is molded into back silicon mold half 102. A back vent 120 is molded into back silicon mold half 102 behind a recess for electrode tab 114.

Figure 2:
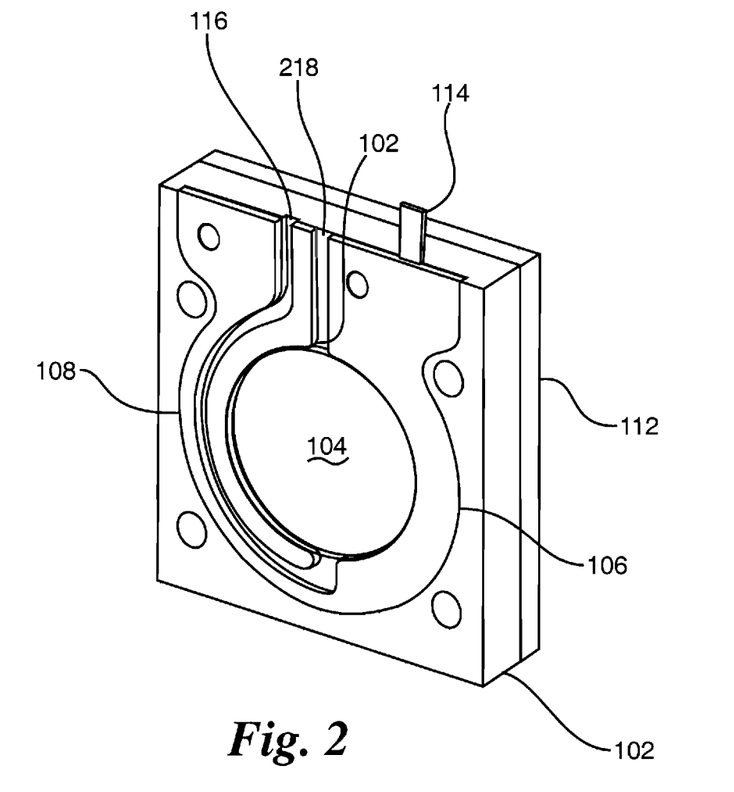
FIG. 2 is an assembled view of the back of the injection mold and sensor cell of FIG. 1.

FIG. 2 is an assembled view of the back half of injection mold and sensor cell 400 showing back silicon mold half 102, TEFLON inserts 106 and 108, back copper electrode 110, aluminum back plate 112 and back electrode tab 114. This view more clearly shows how injection port 116 is formed in-between inserts 106 and 108, along with mold half 112. A gas outlet or vent opening 218 is similarly formed between inserts 106 and 108 for venting from the sample cavity.

Figure 3:
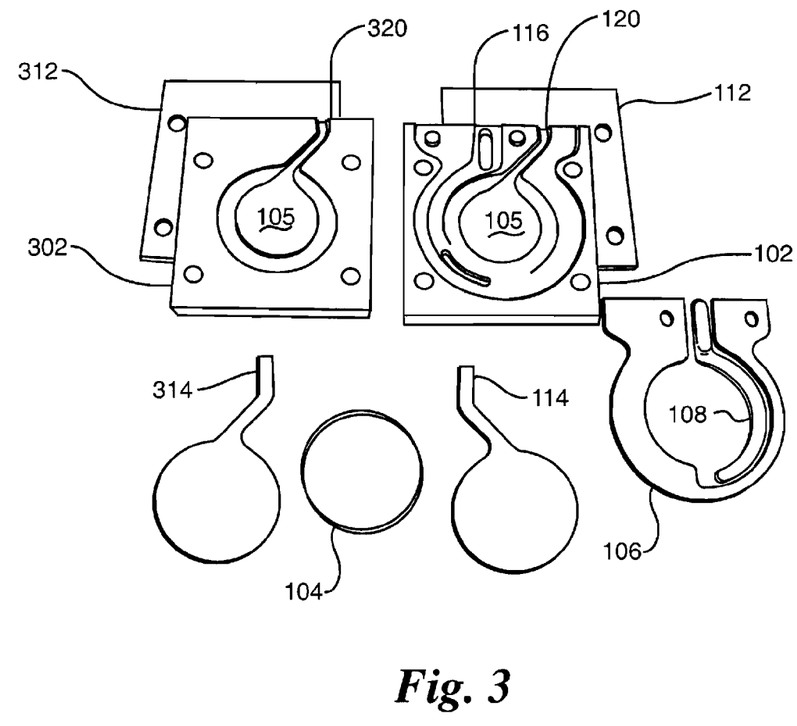
FIG. 3 is a disassembled view of the individual components of the injection mold and sensor cell of FIG. 1.

FIG. 3 shows the disassembled individual components of injection mold and sensor cell 400 for holding a nanocomposite sample 104. Shown are back silicon mold half 102 and front silicon mold half 302; sample 104, TEFLON inserts 106 and 108, back copper electrode 110 and front copper electrode 310; back reinforcing plate 112 and front reinforcing plate 312; back electrode tab 114 and front electrode tab 314; injection ports 116; sample cavity vent openings 218 and 318; and, back vent 120 and front vent 320.

FIG. 4 shows a fully assembled injection mold and sensor cell 400.

Figure 5:
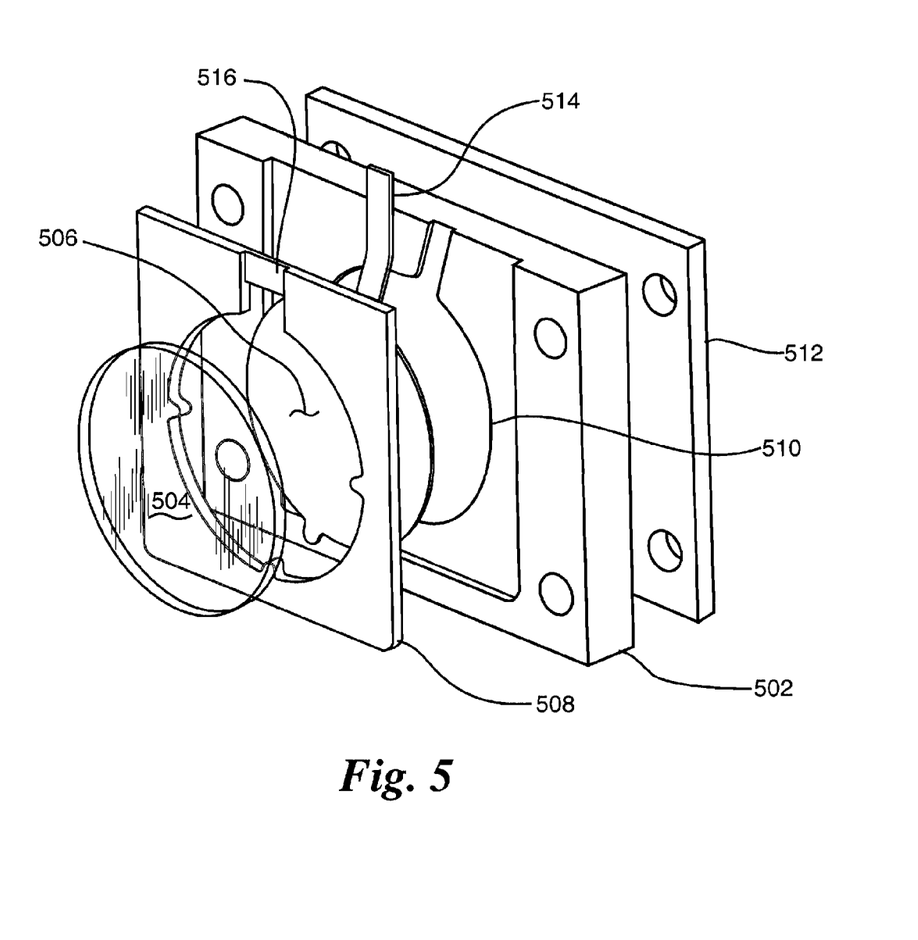
FIG. 5 is an exploded view of the back half of an example embodiment of a compression mold and sensor cell according to the teachings of the present invention.
Figure 8:
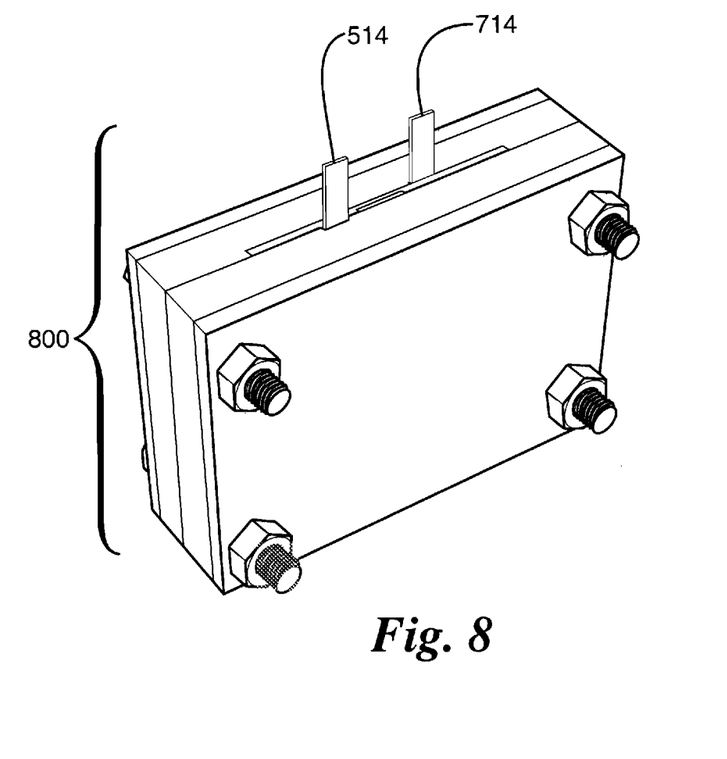
FIG. 8 is an assembled view of the compression mold and sensor cell of FIG. 1.

FIG. 5 is an exploded view of an example embodiment of the back half of a compression mold and sensor cell 800, shown fully assembled in FIG. 8. The back half comprises a back silicon mold half 502 for holding a nanocomposite sample 504 in a sample cavity 506 formed inside TEFLON insert 508. An aluminum reinforcing back plate 512 provides structural support. A back copper electrode 510 contacts the back of sample 504, includes an electrode tab 514 and fits into a recess molded into back silicon mold half 502. TEFLON insert 508 includes a cutout for a vent 516.

Figure 6:
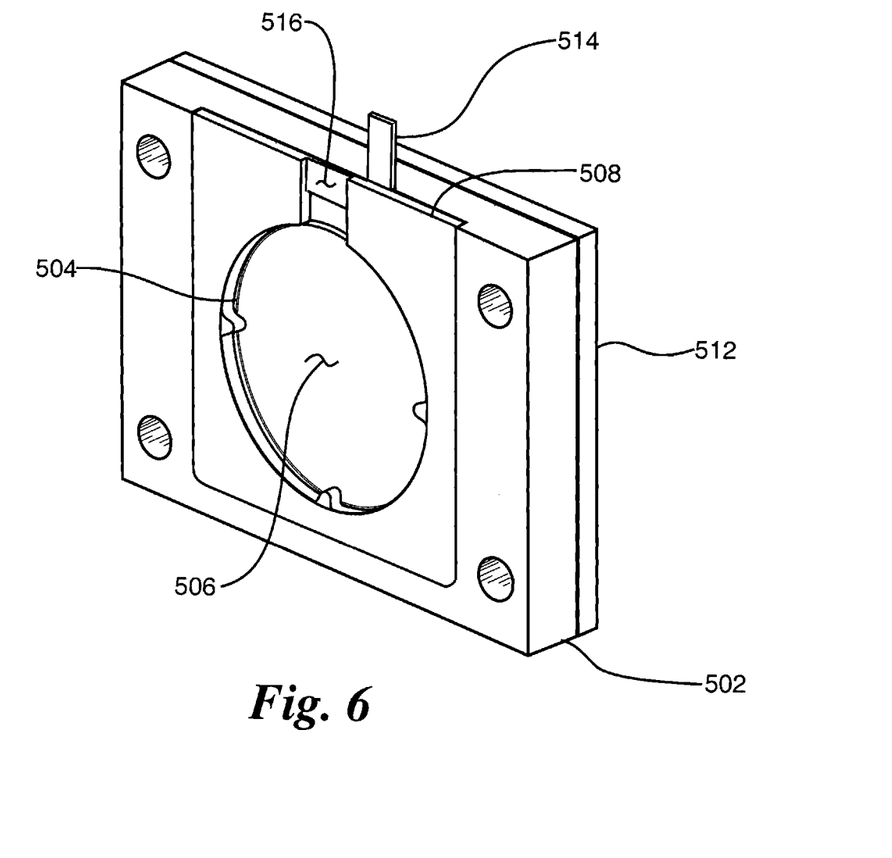
FIG. 6 is an assembled view of the back half of the compression mold and sensor cell of FIG. 5.

FIG. 6 is an assembled view of the back of compression mold and sensor cell 800 showing back silicon mold half 502, cavity 506, TEFLON insert 508, reinforcing back plate 512, back electrode 510, electrode tab 514 and vent cutout 516.

Figure 7:
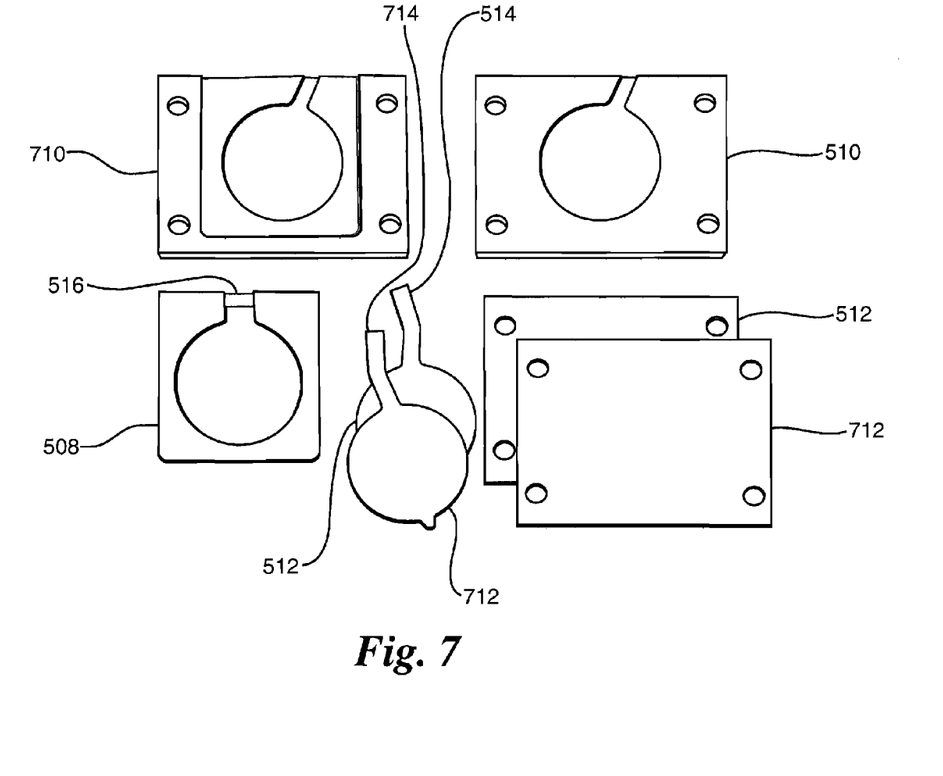
FIG. 7 is a disassembled view of the individual components of the compression mold and sensor cell of FIG. 5.

FIG. 7 shows the disassembled individual components of compression mold and sensor cell 800. Shown are silicon mold halves 510 and 710; TEFLON insert 508; back copper electrode 512 and front copper electrode 712; electrode tabs 514 and 714; vent cutout 516; and, front and back reinforcing back plates 710 and 510.

FIG. 8 shows the entire fully assembled compression mold and sensor cell 800.

The design requirements for the described sensor and mold combinations, or sample cells as they are usually called, are quite stringent. The cells must be made of a material that will withstand extremely hot temperatures (up to ~200° C.) without sustaining irreversible damage, or suffering dimensional distortions that result in non-cylindrical sample molding. While maintaining a well defined cavity for molding materials that change from liquid to glass, the cell must also hold embedded metal electrodes for capacitive impedance spectroscopy and optional high-voltage electric field actuation; therefore, it must be made of an electrically insulating material and possess a reasonable level of thermal conductivity. The cell must be easy to connect to the signal line inside the pressure vessel and be robust enough to provide repeated use. Other important considerations are ease of assembly and disassembly, cleaning and loading of sample material.

Commonly, for the first type injection sensor molds, thermosetting materials are mixed and pre-processed using ultrasound mixing (sonification) and de-gassing, producing a low-viscosity pre-cure suspension that flows like warm honey prior to cure processing. This enables the material to be injected using a syringe without a needle. During development and testing, a nanoclay/epoxy/amine nanocomposite suspension was injected into a sample cell using disposable 5 cc plastic syringes. Copper electrodes, such as electrodes 110 and 310 in FIGS. 1-5, lay in special recessed areas of the mold. Small cavities are placed behind the electrodes and vent at the top of the mold to minimize the compression effect resulting from thermal expansion of the silicone which may otherwise cause the electrodes to bellow, thus producing samples with irregular thickness. Using TEFLON inserts, the electrodes are separated by a constant distance dictated by a desired sample thickness. Electrode tabs, such as tabs 514 and 714 in FIGS. 1-5, extend from the copper electrodes to the exterior of the cell, providing electrical connectivity to sensor signal lines and are terminated with gold coated female crimp connectors slid directly onto the copper tabs. The gold coating makes a reliable and repeatable sensor connection. Aluminum plates on the front and back exterior faces of the mold provide reinforcement, facilitate a liquid-tight seal, and help to distribute and conduct heat uniformly into the sample cell. Prior to sample loading, the silicone and electrode surfaces are minimally treated with a mold release spray, EPDXEASE from Slide Products. This allows the mold to be easily cleaned, the electrodes to be reused, and the cured sample to be nondestructively recovered.

The mold material used during development and testing was RHODORSIL V-240 silicone rubber from Bluestar Silicones. The cured silicone material is light grey in color and has the following properties: 60 Shore A hardness; −54 to 204° C. temperature range; 3.2 dielectric constant (1 kHz) at room temperature; and, high volume resistivity $1.6 \times 10^{15}$ Ω-cm.

The second type compression sensor cell was developed for highly preprocessed thermoset pre-cure materials that are solid at room temperature. These materials cannot be easily injected (even at elevated temperatures) into a sensor cell because of their high viscosity. The pre-cure material can usually be melted and easily compressed into a desired shape using a hot air gun. Again, the sample cell design starts with a simple two part silicone mold with embedded electrodes. The material is compressed into the desired cylindrical shape prior to processing. The cell loading procedure comprises: (a) placing a TEFLON insert with a cylindrical sample cutout onto a silicone block; (b) placing solidified pieces of pre-processed material within the sample cutout; (c) heating the material evenly until it uniformly melts and relaxes into the desired shape; (d) adding or removing material as needed to completely fill the cavity formed by the TEFLON insert; (e) pressing a silicone block on top of the molten material and allowing any excess material to squeeze out of the top tab; (f) allowing the material to cool and solidify; and, (g) removing the silicone blocks. The TEFLON insert, with the preformed sample uniformly supported within the sample cavity, is then ready for cure processing.

The TEFLON and sample unit is neatly inserted into the silicone mold with embedded electrodes present. The electrodes overlap the TEFLON to create a built-in spacer for uniform sample thickness. A thin cutout at the top of the TEFLON insert provides a gas vent and sample overflow pathway. On initial heating during cure processing, the thermoset material melts between the electrodes establishing intimate electrical contact with minimal air entrapment.

The teachings of the disclosed new and improved sample cells will find application in other areas of material processing involving both different processes and different materials.

Those with skill in the art of the invention will readily see that the invention is not limited to the specific materials and dimensions described as part of the example embodiments. Other various modifications to the invention as described may be made, as might occur to one with skill in the art of the invention, within the scope of the claims. Therefore, all contemplated embodiments have not been shown in complete detail. Other embodiments may be developed without departing from the spirit of the invention or from the scope of the claims.

I claim:

1. A sample cell, comprising:
   (a) a cell housing;
   (b) a pair of spaced electrodes embedded inside the cell housing;
   (c) a sample cavity between a front face of each of the spaced electrodes for holding a material sample;
   (d) an expansion cavity behind a back face of at least one of the spaced electrodes; and,
   (e) a vent channel from the expansion cavity to the outside of the cell housing.

2. A sample cell, comprising:
   (a) a cell housing having a top and a bottom;
   (b) a pair of spaced electrodes embedded inside the cell housing;
   (c) a sample cavity between a front face of each of the spaced electrodes for holding a material sample;
   (d) an injection channel through the cell housing from the top of the cell housing into the bottom of the cavity; and,
   (e) a separator between the spaced electrodes, wherein the injection channel is formed within the separator.

3. The sample cell of claim 2, wherein the separator comprises two pieces and the injection channel is formed between the two pieces.

4. The sample cell of claim 2, further comprising:
   (a) an expansion cavity behind a back face of at least one of the spaced electrodes; and,
   (b) a vent channel from the expansion cavity to the outside of the cell housing.

* * * * *